US012796632B2

(12) United States Patent
Lim et al.

(10) Patent No.: US 12,796,632 B2
(45) Date of Patent: Nov. 17, 2026

(54) MEDICAL HEMP CULTIVAR PINKPEPPER AND PRIMER SET COMPOSITION FOR IDENTIFYING THE SAME

(71) Applicants: KNU-INDUSTRY COOPERATION FOUNDATION, Gangwon-do (KR); CHUNCHEON BIOINDUSTRY FOUNDATION, Gangwon-do (KR)

(72) Inventors: Jung Dae Lim, Gangwon-do (KR); Young Seok Lim, Gangwon-do (KR); Byeong Ryeol Ryu, Gangwon-do (KR); Gyeong Ju Gim, Jeollabuk-do (KR); Tae Hyung Kwon, Gangwon-do (KR); Joon Hee Han, Gangwon-do (KR)

(73) Assignees: KNU-INDUSTRY COOPERATION FOUNDATION, Gangwon-do (KR); CHUNCHEON BIOINDUSTRY FOUNDATION, Gangwon-do (KR)

( * ) Notice: Subject to any disclaimer, the term of this patent is extended or adjusted under 35 U.S.C. 154(b) by 178 days.

(21) Appl. No.: 18/586,963

(22) Filed: Feb. 26, 2024

(65) Prior Publication Data

US 2024/0292800 A1 Sep. 5, 2024

(30) Foreign Application Priority Data

| | | |
|---|---|---|
| Mar. 3, 2023 | (KR) | 10-2023-0028214 |
| Jul. 13, 2023 | (KR) | 10-2023-0091043 |
| Jan. 30, 2024 | (KR) | 10-2024-0013874 |

(51) Int. Cl.
*A01H 6/28* (2018.01)
*A01H 5/02* (2018.01)

(52) U.S. Cl.
CPC ................ *A01H 6/28* (2018.05); *A01H 5/02* (2013.01)

(58) Field of Classification Search
None
See application file for complete search history.

(56) References Cited

U.S. PATENT DOCUMENTS 10,888,059 B1 * 1/2021 Reel ........................ A01H 5/02

FOREIGN PATENT DOCUMENTS

KR 10-2269816 B1 6/2021
KR 10-2346700 B1 12/2021

* cited by examiner

*Primary Examiner* — Cynthia E Collins
(74) *Attorney, Agent, or Firm* — The PL Law Group, PLLC

(57) ABSTRACT

A new hemp cultivar Pinkpepper (*Cannabis sativa* L. cv. Pinkpepper) plant deposited under Accession Number KACC 88008BP has a higher content of cannabinoids than the seed and pollen parents. The new hemp cultivar Pinkpepper (*Cannabis sativa* L. cv. Pinkpepper) plant can be advantageously used as hemp for medical purpose, or obtaining hemp seeds or fibers.

5 Claims, 6 Drawing Sheets

Specification includes a Sequence Listing.

| 18-1 Line propagated through cutting and planting process | 18-1 Line propagated through micropropagation process |
| --- | --- |
|  |  |
| Above cutted 18-1 line cultured under smart farm conditions | Inflorescence portion of Pinkpepper |
|  |  |

MEDICAL HEMP CULTIVAR PINKPEPPER AND PRIMER SET COMPOSITION FOR IDENTIFYING THE SAME

CROSS-REFERENCE TO RELATED APPLICATION AND CLAIM OF PRIORITY

This application claims the benefit under 35 USC § 119 of Korean Patent Application Nos. 10-2023-0028214 filed on Mar. 3, 2023, 10-2023-0091043 filed on Jul. 13, 2023, 10-2024-0013874 filed on Jan. 30, 2024 in the Korean Intellectual Property Office (KIPO).

REFERENCE TO AN ELECTRONIC SEQUENCE LISTING

A sequence listing electronically submitted on Feb. 26, 2024 as a XML file named 20240226_S30924GR03_TU_SEQ.XML, created on Feb. 22, 2024 and having a size of 23,909 bytes, is incorporated herein by reference in its entirety.

BACKGROUND

1. Technical Field

The present invention relates to new medical hemp cultivar Pinkpepper (*Cannabis sativa* L. cv. Pinkpepper) and a primer set composition for identifying the same.

This work was supported by the project of Support for Regional Research, Development, and Innovation (R&D) of Ministry of Science and ICT, South Korea (Project No: 2021-DD-UP-0379-01).

2. Background Art

Hemp (*Cannabis sativa* L.) is an annual herbaceous plant in the *Cannabis* genus of Cannabaceae family, and it is classified into three subspecies: *C. sativa* subsp. *sativa, C. sativa* subsp. *indica*, and *C. sativa* subsp. *ruderalis*. Cannabinoids, the collective term for hemp-specific terpene-derived metabolites, encompass over 113 different substances. Among the prominent cannabinoids are Δ9-tetrahydrocannabinolic acid (THCA) and cannabidiolic acid (CBDA), which are characterized by being naturally degraded into the active forms like tetrahydrocannabinol (THC) and cannabidiol (CBD) upon heat exposure. THC can induce undesirable effects such as hallucinations and possesses addictive properties. In contrast, CBD is known for its therapeutic effects like analgesic, anxiolytic, and anticonvulsant properties, making it useful as various therapeutic agents for treating medical conditions including epilepsy.

For medical purposes, hemp has been legalized in over 50 countries including Canada, several states of the United States, Australia, and Japan. Products containing CBD are also sold as functional health food products. In South Korea, a bill allowing the use of medical hemp was passed in November 2018. The Ministry of Food and Drug Safety in South Korea has approved four medicinal products containing hemp components, with Epidiolex (effective component: CBD) being primarily used as a therapeutic agent for epilepsy.

In July 2020, Andong in Gyeongsangbuk-Do, South Korea was designated as a 'Industrial Hemp Regulation-Free Zone', allowing for the production and processing of medical hemp. Generally, hemp is defined as having a THC content of less than 0.3% of the total dry weight of the *Cannabis sativa* L. plant material.

The World Health Organization (WHO) has recommended excluding medical *Cannabis sativa* L. from narcotic classifications, citing its very low addiction and dependence potential. The UN Commission on Narcotic Drugs also excluded *Cannabis sativa* L. from narcotics at the end of 2020. However, in South Korea, current laws classify all products produced from *Cannabis sativa* L. plant or their resin as narcotics. Accordingly, there have been concerns that if the designation of the industrial hemp regulation-free zone is not extended, the businesses may be forced to cease the operations. Meanwhile, in January 2021, there were also proposals to amend certain parts of the "Narcotics Control Act" to legalize medical *Cannabis sativa* L. businesses and allow for both medical and industrial uses.

Traditional domestic resources of *Cannabis sativa* L. in South Korea are primarily cultivated for fiber production, as they mostly exhibit low level of CBD content. Therefore, the present invention aims to develop a new *Cannabis sativa* L. cultivar with high level of CBDA and/or CBD to enhance its utility for medical and industrial purposes.

Meanwhile, Korean Patent Registration No. 2346700 discloses "Method for mass-producing high levels of cannabidiol from *Cannabis sativa* L.", and Korean Patent Registration No. 2269816 discloses "Composition containing hemp extract as an active ingredient for suppressing cancer, reducing anticancer side effect, and inhibiting cancer metastasis". However, there is no mention of "new medical hemp cultivar Pinkpepper and a primer set composition for identifying the same" as described in the present invention.

SUMMARY

The present invention is devised under the circumstances that are described in the above. Specifically, to develop a new medical *Cannabis* (i.e., hemp) cultivar having high content of cannabidiol (CBD) and suitable for smart farm cultivation, which is simultaneously, for a seed use, a short-stem species that can be mechanically harvested in greenhouses or open fields as well as an autoflowering cultivar allowing two cultivations per a year, the inventors of the present invention first set, among the overseas hemp resources collected, genetic resources which exhibit pink color at the time of inflorescence appearance and have high leaf and inflorescence yield, high node numbers for enabling rapid cutting and planting and in vitro propagation, and distinct cannabinoid content, growth conditions like plant height, and sensitivity to daylight length as pollen parent and seed parent, respectively. Subsequently, the pollen parent and seed parent were subjected to artificial crossing using traditional hybridization method, and the inventors identified a new hemp F1 line which has higher content of cannabidiolic acid (CBDA), i.e., a precursor of CBD, in the inflorescence and leaves than that of the seed and pollen parents and, by having plant height and cultivation characteristics suitable for cultivation in open fields, greenhouses, and smart farms, can be mechanically harvested and also, not being affected by flowering daylight length conditions due to the autoflowering characteristics, can be cultivated twice a year under natural conditions. The present invention is completed accordingly, and the aforementioned hemp line is named 'Pinkpepper (*Cannabis sativa* L. cv. Pinkpepper)'.

To achieve the object described in the above, the present invention provides new hemp cultivar Pinkpepper (*Cannabis sativa* L. cv. Pinkpepper) plant obtained through artificial crossing between KHV2 genetic resource as a seed parent and India genetic resource as a pollen parent, with a higher content of cannabinoids than the seed and pollen parents and Accession Number KACC 88008BP.

The present invention further provides a progeny plant derived from the above new hemp cultivar Pinkpepper plant.

The present invention further provides a feminized seed obtained by induction of male flowers on female plant of the above new hemp cultivar Pinkpepper plant, as well as hempseed oil or seed protein derived from the feminized seed.

The present invention further provides a $F_1$ hemp plant produced by crossing the new hemp cultivar Pinkpepper plant with other hemp cultivar, and a seed of the $F_1$ hemp plant.

The present invention further provides hempseed oil or a seed protein derived from the seed of the $F_1$ hemp plant.

The present invention further provides a transgenic hemp plant obtained by transformation of the new hemp cultivar Pinkpepper plant.

The present invention further provides a mutant plant obtained by treating the new hemp cultivar Pinkpepper plant with mutagen.

The present invention still further provides a functional health food composition, a pharmaceutical composition, and a cosmetic composition comprising an extract of the new hemp cultivar Pinkpepper plant as effective component.

The present invention further provides a primer set composition for identifying new hemp cultivar Pinkpepper or a progeny plant thereof, comprising one or more oligonucleotide primer sets selected from the group consisting of the oligonucleotide primer set of SEQ ID NOs: 7 and 8; and the oligonucleotide primer set of SEQ ID NOs: 9 and 10.

The present invention further provides a kit for identifying new hemp cultivar Pinkpepper or a progeny plant thereof, including the primer set composition as described above and a reagent for carrying out an amplification reaction.

The present invention still further provides a method for identifying new hemp cultivar Pinkpepper or a progeny plant thereof, the method comprising: extracting genomic DNA from a hemp plant; amplifying a target sequence by having the genomic DNA separated above as template and carrying out an amplification reaction using the primer set composition of the present invention; and detecting a product of the amplification step.

Pinkpepper as a new hemp cultivar according to the present invention is a medical hemp having a plant height suitable for harvesting in smart farms, vigorous growth characteristics, and excellent content of cannabinoid components having medical efficacy. It is also a short-stem species that can replace the cultivars traditionally used for obtaining seeds, and has many branches and a high seed yield due to its autoflowering characteristics that allow two cultivations per year, so it is expected to be advantageously used in the related industries.

BRIEF DESCRIPTION OF THE DRAWINGS

FIG. 4A to FIG. 4I are the electrophoresis results of PCR products using primer sets of InDel1 to InDel9 in order. Lane 1: Pinkpepper, Lane 2: Critical +2.0, Lane 3: Cinderella story, Lane 4: Cherry blossom, Lane 5: Cloud berry, Lane 6: Chungsam, and Lane 7: Pinkpepper×Chungsam $F_1$ generation (open pollinated), marker: 100 bp.

DETAILED DESCRIPTION

Figure 1:
FIG. 1 shows artificial selective crossing for the development of new hemp cultivar.
Figure 2:
FIG. 2 shows the whole plant form of the Pinkpepper (line name 18-1) $F_1$ line grown in the open field (top) or in the house (bottom).
Figure 3:
FIG. 3 shows cutting and planting culture (top left) and in vitro culture (top right) for maintaining the new cultivar Pinkpepper (line 18-1), and Pinkpepper plant being cultivated in a smart farm (bottom left) and the inflorescence of Pinkpepper (bottom right).
Figure 3:
Figure 3:
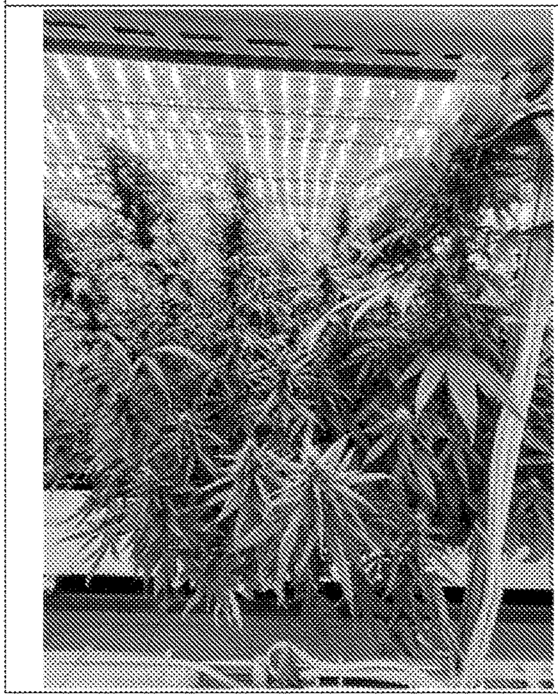
Figure 3:
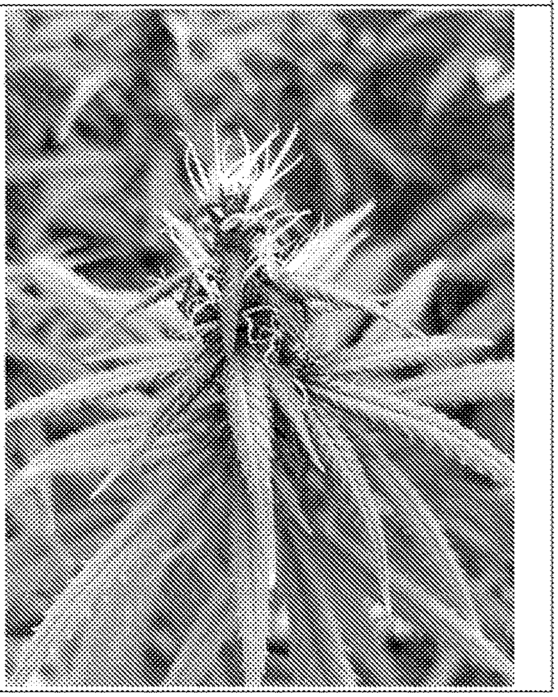

To achieve the purpose of the present invention, the present invention provides new hemp cultivar Pinkpepper (*Cannabis sativa* L. cv. Pinkpepper) plant obtained through artificial crossing between KHV2 genetic resource as a seed parent(female) and India genetic resource as a pollen parent (male), with a higher content of cannabinoids than the seed and pollen parents and Accession Number KACC 88008BP.

The *Cannabis sativa* L. cv. Pinkpepper was duly deposited with the Korean Agricultural Culture Collection (KACC) (having the address of 166 Nongsaengmyeon-ro, 1seo-myeon, Wanju-gun, Jeollabuk-do 55365, 55365, Republic of Korea) under the Access number of KACC 88008BP on May 26, 2023. The deposit has been made under the terms of the Budapest Treaty and all restrictions imposed by the depositor on the availability to the public of the biological material will be irrevocably removed upon the granting of a patent.

The present invention further provides a progeny plant derived from the above new hemp cultivar Pinkpepper plant.

With regard to the Pinkpepper plant according to the present invention, the cannabinoids whose content is higher than that of the seed and pollen parents may be cannabidiolic acid (CBDA) and cannabidiol (CBD), but are not limited thereto. The CBDA is decomposed into cannabidiol (CBD) by heat.

The new hemp cultivar Pinkpepper according to the present invention is characterized in that, under smart farm conditions, the total cannabidiol content is increased to 2.6493% in leaves and 11.7026% in inflorescence compared to the seed and pollen parents and, in open field conditions, the total cannabidiol content is increased to 3.3870% in leaves and 11.8684% in inflorescence compared to the seed and pollen parents. Furthermore, the Pinkpepper plant shows a plant height of about 2 meters in open field cultivation, and a plant height of about 1 meter in smart farm cultivation using nutrient media solution, and thus it exhibits growth characteristics that have a height suitable for open field and smart farm cultivation facilities without requiring any additional processing.

The Pinkpepper plant according to the present invention has the plant height characteristics of the pollen parent and the autoflowering (i.e., allowing two cultivations per year) and high CBD content traits of the seed parent. In addition, not only does it have a large number of branches and inflorescences, but it is also a bush type, making it suitable for high-yield cannabinoid production. Additionally, the stems have the characteristic of containing high levels of anthocyanins.

The hemp genetic resource of KHV2 (CBD Paqle Kush Auto flowering) used as the seed parent in the present invention is an overseas hybrid having genetic composition of *C. sativa* subsp. *indica:C. sativa* subsp. *sativa:C. sativa* subsp. *ruderalis*=70:10:20(%), and India used as the pollen parent is a hemp genetic resource native to India, and both are characterized by having higher CBD content than THC.

The Pinkpepper 'plant' of the present invention includes both the whole plant or part of the plant. The 'part' of the plant according to the present invention may include, although not limited thereto, inflorescences, leaves, roots, stems, or the like of the new hemp cultivar Pinkpepper. Additionally, the progeny plant derived from the Pinkpepper plant may be a seedling-type progeny plant derived through asexual reproduction of the new hemp cultivar Pinkpepper, but is not limited thereto. The asexual reproduction method may include, but is not limited to, plant tissue culture techniques such as cell culture, protoplast culture, chemical culture, and callus culture.

In the case of hemp, due to the nature of the species, it is divided into female plant and male plant, or both male and female flowers appear on the same plant at the same time. Thus, in order to maintain the variety characteristics, male and female flowers are grown separately and the female flowers are chemically treated to produce female seeds, or the hybrid $F_1$ generation line is cultivated so that the excellent lines can be maintained through vegetative propagation.

Through the cultivation based on nodal culture or cutting and planting, the new hemp cultivar Pinkpepper according to the present invention can be maintained as the plant itself without any genetic mutation.

By using KHV2 genetic resource as seed parent and India genetic resource as pollen parent, the inventors of the present invention obtained, through artificial crossing, a hemp line with higher cannabinoid compared to the seed and pollen parents, and they named the line "Pinkpepper (*Cannabis sativa* L. cv. Pinkpepper)". Then, its feminized seeds were taken as representative sample and deposited in the Korean Agricultural Culture Collection (KACC) on May 26, 2023 (Accession Number: KACC 98136P), and an international deposit number was assigned on Dec. 13, 2023. (Accession Number: KACC 88008BP).

The present invention further provides a feminized seed obtained by induction of male flowers on female plant of the above new hemp cultivar Pinkpepper plant, as well as hempseed oil or seed protein derived from the feminized seed.

The sex of hemp is determined by X and Y sex chromosomes of a pollen. Pollen of a male plant consists of female pollen with n=9+X and male pollen with 9+Y. The stigma plant pollinated with female pollen becomes a female plant and the stigma plant pollinated with male pollen becomes a male plant. As such, if the sex of the female plant, which normally has somatic sex chromosome composition of XX, is altered to induce male traits, the pollen from this plant will contain only X chromosomes. By cross-pollinating this with a regular female plant, the resulting seeds, modified in this manner, will become 'feminized seeds' that yield only females with 100% certainty. This can significantly enhance the efficiency of breeding and seed collecting.

In the present invention, the induction of male traits in the aforementioned female hemp plant can be accomplished through methods that are well known in the pertinent art, such as change in daylight hours or treatment with silver nitrate during the vegetative growth stage.

Hemp seeds (i.e., achenes) contain a large amount of unsaturated fatty acids, and hemp oil, in particular, contains γ-linolenic acid (GLA), and thus showing preventive or therapeutic effects on skin aging, atopic dermatitis, cardiovascular diseases, rheumatoid arthritis, and others.

The present invention further provides a $F_1$ hemp plant produced by crossing the new hemp cultivar Pinkpepper plant with other hemp cultivar, as well as a seed of the $F_1$ hemp plant. The crossing may be performed according to methods related to plant breeding that are known to those skilled in the pertinent art and, since the new hemp cultivar Pinkpepper according to the present invention is characterized by having a high content of cannabinoid components having medical efficacy, the Pinkpepper plant can be used as a seed parent material for breeding new varieties of hemp, especially medical hemp, but it is not limited to this. The $F_1$ hemp plant includes the whole plant, part of the plant, and progeny plant derived therefrom.

The present invention further provides hempseed oil or a seed protein derived from the seed of the $F_1$ hemp plant.

The present invention further provides a transgenic hemp plant obtained by transformation of the new hemp cultivar Pinkpepper plant, as well as a transgenic seed of the transgenic hemp plant. The transformation method can be accomplished through various techniques that are known in the pertinent art, and the transgenic hemp plant according to the present invention includes all transgenic plants having the genetic background of Pinkpepper plant.

The present invention further provides a mutant plant obtained by treating the new hemp cultivar Pinkpepper plant with mutagen. The mutagen includes physical mutagens such as X ray, γ ray ($^{60}Co$), β ray ($^{32}P$, $^{35}S$, or the like) and neutron beam and chemical mutagens such as proflavin, acridine orange, N-methyl-N'-nitro-N-nitrosoguanidine (NTG or MNNG), 4-nitrogyinoline 1-oxide (4-NQO), nitrous acid ($HNO_2$), hydroxylamine ($NH_2OH$), dimethylsulfate (DMS), diethylsulfate (DES), ethyl ethanesulfonate (EES), methyl methanesulfonate (MMS), and ethyl methanesulfonate (EMS), but is not limited thereto.

The present invention further provides a functional health food composition comprising an extract of the new hemp cultivar Pinkpepper plant as effective component.

With regard to the functional health food composition according to the present invention, the new hemp cultivar Pinkpepper is, as a medical hemp, characterized by having a high content of medically beneficial cannabinoid compounds (CBD, CBDA). The extract of the Pinkpepper may be obtained by extracting a part, a seed, or the like of the Pinkpepper plant with an extraction solvent selected from the group consisting of water, $C_1$ to $C_6$ lower alcohols, and mixtures thereof, but it is not limited thereto. Additionally, the extraction method may utilize all conventional methods that are well known in the art, including filtration, hot water extraction, immersion extraction, reflux cooling extraction, and ultrasound extraction.

The term "extract" used in this specification generally has a meaning that is commonly known in the pertinent art as a crude extract, but, in a broad sense, it also encompasses fractions that are obtained by further fractionating the extract. In other words, the extract includes not only those obtained using the aforementioned extraction solvents but also those obtained by applying additional purification processes. For instance, fractions obtained by additionally performing various purification processes such as passing the aforementioned extract through an ultrafiltration membrane having certain molecular weight cut-off or separations performed by various chromatography techniques (designed for separation based on size, charge, hydrophobicity, or affinity) are also included in the extract of the present invention.

The functional health food composition of the present invention is preferably manufactured in any one of the formulation forms selected from powder, granules, pill, tablet, capsule, candy, syrup, and beverage, but it is not limited thereto.

When using the functional health food composition of the present invention as a food additive, the extract of the new hemp cultivar Pinkpepper can be added directly or used in combination with other foods or food ingredients, and it can be appropriately used according to common methods. The amount of the active ingredient can be appropriately determined depending on their intended use (e.g., prevention, health, or therapeutic treatment). Generally, when manufacturing food or beverages, the composition of the present invention is added to the raw materials in an amount of not more than 15 parts by weight, preferably not more than 10 parts by weight. However, in cases of long-term consumption for health and hygiene purposes or for managing health, the amount may be less than the aforementioned range, and, since there may be no problem with safety, the active ingredient may also be used in an amount exceeding the aforementioned range.

The present invention further provides a pharmaceutical composition comprising an extract of the new hemp cultivar Pinkpepper plant as effective component.

With regard to the pharmaceutical composition according to the present invention, the new hemp cultivar Pinkpepper is, as a hemp for medical use, characterized by having a high content of cannabinoid components known for their medical efficacy. The extract of the Pinkpepper is as described above.

According to Project CBD, at least 50 symptoms are considered to be improved by cannabidiol (CBD). These symptoms include pain, seizures, muscle spasms, nausea caused by chemotherapy, digestive disorders such as colitis and inflammatory bowel disease, muscle tension, epilepsy, multiple sclerosis, Parkinson's disease, mood disorders, anxiety, post-traumatic stress disorder, and high blood pressure.

The pharmaceutical composition of the present invention may further comprise, other than the effective component described above, a pharmaceutically acceptable carrier, vehicle, or diluent, and it can take various forms for oral or parenteral administration. When formulated, production is made by using commonly-used diluents or vehicles such as fillers, expanders, binders, wetting agents, disintegrants, or surfactants. For solid preparations intended for oral administration, they may include capsules, powders, granules, tablets, pills, etc., and these solid formulations are formulated by mixing one or more compounds with at least one vehicle such as starch, calcium carbonate, sucrose, lactose, gelatin, etc. Additionally, lubricants such as magnesium stearate, talc, etc. can be used in addition to simple vehicles. For liquid preparations intended for oral administration, they may include suspensions, emulsions, syrups, aerosols, etc., and in addition to commonly used simple diluents like water and liquid paraffin, various vehicles such as wetting agents, sweeteners, flavors, preservatives, etc. may be included. For preparations intended for parenteral administration, they may include sterilized aqueous solutions, non-aqueous solvents, suspensions, emulsions, freeze-dried formulations, suppositories, etc. Examples of non-aqueous solvents and solvents for suspension include propylene glycol, polyethylene glycol, vegetable oils such as olive oil, injectable esters such as ethyl oleate, etc. Examples of suppository bases include Witepsol, Macrogol, Tween 61, cocoa butter, laurin, glycerol gelatin, etc. When the pharmaceutical composition is administered parenterally, it is preferable to choose a method like topical application on skin, or an intraperitoneal, rectal, intravenous, intramuscular, subcutaneous, intrathecal, and intracerebrovascular injection method.

The pharmaceutical composition according to the present invention is administered in a pharmacologically effective amount. In the present invention, the expression "pharmacologically effective amount" refers to an amount sufficient to treat a disease with a reasonable benefit/risk ratio applicable to medical therapy. The effective dosage level can be determined based on various factors, including the type and severity of the patient's condition, the activity of the drug, sensitivity to the drug, administration time, route of administration, elimination rate, treatment duration, factors including other drugs that are simultaneously used, and other factors well-known in the medical field. The pharmaceutical composition of the present invention can be administered as an individual therapeutic agent or in combination with other therapeutic agents, sequentially or simultaneously with conventional therapies, and in a single dose or multiple doses. It is important to administer, with consideration of the aforementioned factors, the minimum effective amount that can achieve maximum efficacy without having any adverse effects, and this can be readily determined by a person who is skilled in the pertinent art.

The present invention still further provides a cosmetic composition comprising an extract of the new hemp cultivar Pinkpepper plant as effective component. The aforementioned cosmetic composition can be preferably manufactured in any of the formulations selected from solution, suspension, emulsion, paste, gel, cream, lotion, powder, soap, surfactant-containing cleansing agent, oil, powder foundation, emulsion, foundation, wax foundation, and spray, among others. However, it is not limited thereto.

In the case of the cosmetic composition of the present invention being in the formulation form of a solution or emulsion, solvents, solvent vehicles, or emulsifying agents are used as a carrier component. For example, water, ethanol, isopropanol, ethyl carbonate, ethyl acetate, benzyl alcohol, benzyl benzoate, propylene glycol, 1,3-butylene glycol oil, glyceryl fatty esters, polyethylene glycol, or sorbitan fatty acid esters can be used.

In the case of the cosmetic composition of the present invention being in the formulation form of a suspension, water, ethanol, or propylene glycol as liquid diluents, ethoxylated isostearyl alcohol, polyoxyethylene sorbitol esters, and polyoxyethylene sorbitan esters as suspending agents, and microcrystalline cellulose, aluminum hydroxide, bentonite, agar, or tragacanth can be used.

In the case of the cosmetic composition of the present invention being in the formulation form of a paste, cream, or gel, animal fibers, plant fibers, waxes, paraffin, starch, tragacanth, cellulose derivatives, polyethylene glycol, silicone, bentonite, silica, talc, or zinc oxide may be used as a carrier component. In the case of the cosmetic composition of the present invention being in the formulation form of powder or spray, lactose, talc, silica, aluminum hydroxide, calcium silicate, or polyamide powder can be used as a carrier component. Especially in the case of a spray, a propellant such as chlorofluorohydrocarbons, propane-butane, or dimethyl ether may be additionally included.

In the case of the cosmetic composition of the present invention being in the formulation form of a surfactant-containing cleansing agent, fatty alcohol sulfates, fatty alcohol ether sulfates, sulfosuccinic acid monoester, acethionate, imidazolinium derivatives, methyltaurates, sarcosinates, fatty acid amide ether sulfates, alkylamidobetaines, fatty alcohols, glyceride fatty acids, diethanolamide fatty acids, vegetable oils, lanolin derivatives, or ethoxylated glyceryl fatty acid esters can be used as a carrier component.

The present invention further provides a primer set composition for identifying new hemp cultivar Pinkpepper or a progeny plant thereof, comprising one or more oligonucleotide primer sets selected from the group consisting of the oligonucleotide primer set of SEQ ID NOs: 7 and 8; and the oligonucleotide primer set of SEQ ID NOs: 9 and 10.

With regard to the primer set composition of the present invention, the progeny plant may be a plant derived from a Pinkpepper feminized seed or a $F_1$ plant produced by crossing Pinkpepper plant with other hemp cultivar, but it is not limited thereto.

With regard to the primer set composition according to one embodiment of the present invention, the oligonucleotide primer set of SEQ ID NOs: 7 and 8 and the oligonucleotide primer set of SEQ ID NOs: 9 and 10 are a primer set which can amplify InDel (Insertion and Deletion) mutation region.

With regard to the primer set composition of the present invention, the primer may contain an oligonucleotide composed of a fragment of 16 or more, 17 or more, 18 or more, 19 or more, or 20 or more consecutive nucleotides in the sequence of SEQ ID NOs: 7 to 10, depending on the sequence length of each primer. For example, the primer of SEQ ID NO: 7 (22 oligonucleotides) may contain an oligonucleotide composed of a fragment of 16 or more, 17 or more, 18 or more, 19 or more, 20 or more, or 21 or more consecutive nucleotides in the sequence of SEQ ID NO: 1. Furthermore, the primer may also contain a sequence which has an addition, a deletion, or substitution in the nucleotide sequences of SEQ ID NOs: 7 to 10.

In the present invention, the "primer" refers to a single-stranded oligonucleotide sequence complementary to the nucleic acid strand to be copied, and it can serve as a starting point for the synthesis of a primer extension product. The length and sequence of the primers should allow for initiation of synthesis of the extension product. The specific length and sequence of the primer will depend on the complexity of the DNA or RNA target desired as well as the conditions under which the primer is used, such as temperature and ionic strength.

In the present specification, the oligonucleotide used as primers may also include nucleotide analogues, such as phosphorothioates, alkylphosphorothioates or peptide nucleic acids, or may contain an intercalating agent.

The present invention further provides a kit for identifying new hemp cultivar Pinkpepper or a progeny plant thereof, including the primer set composition as described above and a reagent for carrying out an amplification reaction.

In the kit according to the present invention, the primer set composition and Pinkpepper progeny plant are the same as described above.

In one embodiment of the present invention, the kit may further include a reagent for carrying out an amplification reaction, and the reagent for carrying out the amplification reaction may include DNA polymerase, dNTPs, and a buffer, but it is not limited thereto.

In addition, the kit may additionally include a user guide describing optimal conditions for carrying out the reactions. The guide is a printed material that explains how to use the kit, for example, how to prepare reverse transcription buffer solutions and PCR buffer solutions, and the suggested reaction conditions. Instructions include information leaflets in the form of pamphlets or leaflets, labels affixed to the kit, and instructions on the surface of the package containing the kit. Additionally, the guide includes information disclosed or provided through electronic media such as the Internet.

The present invention still further provides a method for identifying new hemp cultivar Pinkpepper or a progeny plant thereof, the method comprising: amplifying a target sequence by having the genomic DNA separated above as template and carrying out an amplification reaction using the primer set composition of the present invention; and detecting a product of the amplification step.

In the identification method according to the present invention, the primer set composition and Pinkpepper progeny plant are the same as those described in the above.

The identification method of the present invention includes the step of isolating genomic DNA from a hemp plant sample. The hemp plant sample is not limited to this, but may include hemp inflorescence, leaves, roots, stems, etc. Method for isolating genomic DNA from the plant sample can be methods known in the pertinent art. For example, the CTAB (Cetyltrimethylammonium bromide) method can be used, or the Wizard prep kit (Promega) can be used.

The target sequence can be amplified by carrying out an amplification reaction using the isolated genomic DNA as a template and using one or more oligonucleotide primer sets according to an embodiment of the present invention as primer. Method for amplifying target nucleic acids included polymerase chain reaction (PCR), ligase chain reaction, nucleic acid sequence-based amplification, and transcription-based amplification), strand displacement amplification or amplification via QB replicase, and any other suitable method for amplifying nucleic acid molecules that are known in the pertinent art. Among these, PCR is a method of amplifying, using polymerase, a target nucleic acid from a primer pair that specifically binds to the target nucleic acid. The PCR method is well known to a person who is skilled in the art, and commercially available kits can also be used.

In one embodiment of the present invention, the method for identifying the hemp cultivar Pinkpepper or a progeny plant thereof includes detecting the product of the amplification step, and the detection of the product of the amplification step may be performed through gel electrophoresis, DNA chip, radioactivity measurement, fluorescence measurement, or phosphorescence measurement, but it is not limited thereto. As one of the methods for detecting the amplification product, gel electrophoresis can be performed, and gel electrophoresis can use agarose gel electrophoresis or acrylamide gel electrophoresis depending on the size of the amplification product. Additionally, capillary electrophoresis can be performed, and capillary electrophoresis can be performed using, for example, an ABi Sequencer. In addition, the fluorescence measurement method is to perform labeling the 5'-end of the primer with Cy-5 or Cy-3 so that the target sequence is labeled, upon PCR, with a detectable fluorescent labeling substance, and the labeled fluorescence can be measured using a fluorometer. In addition, the radioactivity measurement method involves adding a radioactive isotope such as $^{32}P$ or $^{35}S$ to the PCR reaction solution when performing PCR to label the amplification product, and then, by using a radioactivity measurement device such as a Geiger counter or a liquid scintillation counter, the radioactivity can be measured.

Hereinbelow, the present invention is explained in greater detail in view of Examples. However, the following Examples are given only for exemplification of the present invention and it is evident that the scope of the present invention is not limited by them.

EXAMPLES

Experimental Example 1. Determination of Cannabinoid Content

The present invention was carried out under the approval of the Narcotics Handler (i.e., academic researcher) (Approval Number: Seoul-1806) and Narcotics and Raw Material Handling Approval (Narcotics Policy Department-4789, Narcotics Policy Department-6373, Ministry of Food and Drug Safety, South Korea).

The samples for cannabinoid content analysis were freeze-dried samples, which were stored at 4 °C until extraction. As CBD and $\Delta^9$-THC standards, products from CAYMAN (CAYMAN Co., USA) were used. As a CBDA standard, a product from Cerilliant (Round Rock, USA) was used, and as a $\Delta^9$-THCA standard, a product from Sigma-Aldrich was used. Each standard reagent was diluted to concentrations of 10, 20, 30, 40, and 50 ppm to construct a standard curve. The measured values of the samples were then fitted to the standard curve to calculate the content of each cannabinoid.

After completing the freeze-drying process, 1 g of the sample was weighed and placed in a 50 ml conical tube. Then, 30 ml of methanol with a purity of at least 99.5% were added, followed by sonication using an ultrasonic homogenizer (JEIO TECH Co., Ltd., Korea) at room temperature (25±1 °C) for 30 minutes. The supernatant was then filtered using a 0.45 μm syringe filter and used for HPLC analysis. The content unit (%) of each cannabinoid was expressed as ratio of each cannabinoid relative to dry weight of the corresponding sample.

TABLE 1

HPLC operating condition for the analysis of CBDA, THCA, CBD and THC

| | |
|---|---|
| Instrument | Shimadzu LC-20AT HPLC system |
| Column | Reverse phase Zorbax SB-$C_{18}$ (4.6 mm * 100 mm, 3.5 μm) |
| Detector | UV-VIS detector (275 nm) |
| Solvent | 70% Acetonitrile containing 0.1% phosphoric acid |
| Flow rate | 1.5 ml/min |
| oven | 27 °C |
| Injection volume | 10 μl |
| Elution type | Isocratic |

Example 1. Crossing Process

Inventors of the present invention collected overseas genetic resources (i.e., germplasm) of hemp which has been cultivated for medical and hemp cloth purposes and evaluated its botanical and cultural characteristics. All collected samples of the overseas hemp genetic resources are stored in the Department of Life and Health Engineering at Kangwon National University.

TABLE 2

Plant genetic resources colleted from international site in *C. sativa*.

| Name | Country of origin | Name | Country of origin |
|---|---|---|---|
| India | India | 199571 | China |
| UK 1 | United Kingdom | 199572 | Kazakhstan |
| UK 2 | United Kingdom | 199573 | Afghanistan |
| Spain | Spain | 200318 | Nepal |
| Latvia | Latvia | 207757 | Yugoslavia |
| Singapore | Singapore | 207758 | Yugoslavia |
| Portugal | Portugal | 207758 | Yugoslavia |
| France | France | 207760 | Yugoslavia |
| Lithuania | Lithuania | 207761 | Estonia |
| PURPLE AFGHAN KUSH | USA | 207762 | United Kingdom |
| SHARK SHOCKED CBD (100% DNF) | USA | 207763 | Russia |
| DINAMED CBD (100% DNF) | USA | 207764 | Russia |
| QUICK GORILLA | USA | 207765 | Russia |
| GORILLA AUTO (100% DNF) | USA | 207766 | Russia |
| MOBY DICK XXL AUTO (100% DNF) | USA | 207767 | Russia |
| QUICK DINAMED CBD (100% DNF) | USA | 207768 | USA |
| MOBY DICK (100% DNF) | USA | 207769 | USA |
| CHEESE CBD (AUTO), 100% DNF | USA | 207810 | USA |
| DINAMED CBD PLUS (100% NF) | USA | 209078 | Russia |
| BLUE DREAM CBD | USA | 209079 | Russia |
| Alpine Star CBD Feminized (KHV1) | USA | 209080 | United Kingdom |
| CBD Pagle Kush Auto flowering (KHV2) | USA | 209061 | Russia |
| Charlotte's Web ♀ Seeds (KHV3) | USA | 209082 | Russia |
| Harlequin ♀ seeds (KHVA) | USA | K109453 | Russia |
| MAZAR Auto flowering feminized (KHV5) | USA | K109502 | RUS + Kor |

TABLE 2-continued

| Plant genetic resources colleted from international site in *C. sativa*. | | | |
|---|---|---|---|
| Name | Country of origin | Name | Country of origin |
| Cerry wine | USA | K109510 | RUS + Kor |
| 105982 | China | K133756 | Bulgaria |
| 199568 | China | K153762 | North Korea |
| 199569 | China | K153763 | North Korea |
| 199570 | China | | |

The genetic resources shown in Table 2 were sown in seedling trays (54 cmx 28 cm, 72 wells) containing a mixture of bio-soil (Heungnong Jongmyo Co., Korea) and top-soil (Taeheung F&G, Korea) in a 2:1 ratio. After 2 weeks, they were transplanted into larger pots (diameter 50 cm x depth 70 cm) and cultivated for 8 weeks in a greenhouse with adjustable light conditions (18 h/day light condition, 25±3 °C). After 8 weeks, the light condition was adjusted to 12 h/day, and as soon as male flowers appeared, they were separately cultivated in a room dedicated to male flowers to prevent natural random crossing. When inflorescence appears in all male and female plants, selective breeding was performed by setting seed and pollen parents with no browning, high production of leaves and inflorescence, and a high number of nodes to ensure rapid cutting and plantation and in vitro propagation. There were a total of 34 hemp plants from which $F_1$ generation seeds were obtained through selective crossing.

$F_1$ generation seeds were sown in seedling trays mixed with bio top-soil and top-soil in a 2:1 ratio as described above, then transferred to larger pots after 2 weeks and grown for 8 weeks in a greenhouse with controlled light conditions. Even when the harvest is made from the same individual plant with the same parent stock, each seed had different traits, so each seed was sown separately (for example, seed number 1 obtained from individual plant number 1 was denoted as 1-1). After 8 weeks, the light conditions were adjusted to 12 h/day, and as soon as male flowers appeared, they were separately cultivated in a room dedicated to male flowers to prevent natural crossing and at the same time, plant gender was determined. After the gender determination was completed in all individual plants, the cannabinoid content of the leaves was evaluated, and a morphology study was also conducted (Table 3 and Table 4).

TABLE 3

Evaluation of main cannabinoid and morphological charateristic of F1 generation by selected crossing by artficial pollination.

| Plant name | Plant number | CBDA (%) | CBD (%) | THC (%) | THCA (%) | Gender | Stem diameter (cm) | Plant height (cm) | Leaf Length (cm) | Leaf width (cm) | Branch number |
|---|---|---|---|---|---|---|---|---|---|---|---|
| 1 (I:P) | 2 | 0.0749 | 0.0008 | 0.0010 | 0.0782 | ♀ | 0.56 | 110 | 27 | 4.00 | 7 |
| | 3 | 0.2558 | 0.0013 | 0.0028 | 0.0772 | ♀ | 0.71 | 90 | 18 | 3.50 | 15 |
| 2 (I:U1) | | | | | Not germinated | | | | | | |
| 3 (I:U2) | | | | | Not germinated | | | | | | |
| 4 (I:La) | | | | | Not germinated | | | | | | |
| 5 (I:La) | 1 | 0.0026 | 0.0005 | 0.1491 | 0.1304 | ♂ | 0.84 | 148 | 26 | 4.00 | 24 |
| 6 (I:La) | | | | | Not germinated | | | | | | |
| 7 (I:La) | | | | | Not germinated | | | | | | |
| 8 (I:P) | 1 | 0.1504 | 0.0008 | 0.0019 | 0.0786 | ♀ | 0.72 | 138 | 21 | 4.00 | 17 |
| | 2 | 0.1220 | 0.0012 | 0.0020 | 0.1037 | ♀ | 0.62 | 134 | 23 | 4.50 | 13 |
| | 3 | 0.2026 | 0.0015 | 0.0022 | 0.0821 | ♀ | 0.73 | 107 | 24 | 4.00 | 12 |
| 9 (I:P) | | | | | Not germinated | | | | | | |
| 10 (I:P) | 1 | 0.2489 | 0.0006 | 0.0373 | 0.0961 | ♀ | 1.03 | 200 | 30 | 7.00 | 20 |
| | 2 | 0.2317 | 0.0002 | 0.0370 | 0.1074 | ♀ | 0.83 | 190 | 33 | 7.00 | 14 |
| | 3 | 0.4757 | ND | 0.1097 | 0.1155 | ♀ | 1.03 | 170 | 36 | 6.00 | 16 |
| | 4 | 0.0038 | ND | 0.0537 | 0.1115 | ♀ | 0.93 | 170 | 29 | 5.00 | 0 |
| | 5 | 0.0041 | 0.0013 | 0.1448 | 0.1265 | ♀ | 0.85 | 150 | 30 | 6.00 | 14 |
| 11 (U2:P) | | | | | Not germinated | | | | | | |
| 12 (I:La) | 1 | 0.1006 | 0.0312 | 0.0173 | 0.2177 | ♂ | 0.60 | 158 | 21 | 3.50 | 22 |
| | 2 | 0.3682 | 0.0306 | 0.0059 | 0.1185 | ♀ | 0.60 | 149 | 18.5 | 3.00 | 12 |
| | 3 | 0.1607 | 0.0286 | 0.0273 | 0.1596 | ♂ | 0.55 | 154 | 24 | 3.00 | 24 |
| | 4 | 0.3069 | 0.0118 | 0.0378 | 1.2970 | ♀ | 0.50 | 142 | 19 | 4.00 | 17 |
| | 5 | 0.1567 | 0.0011 | 0.0276 | 0.0608 | ♀ | 0.60 | 143 | 22 | 3.20 | 16 |
| 13 (I:P) | 1 | 0.3052 | 0.0135 | 0.0509 | 0.1377 | ♀ | 0.80 | 180 | 28 | 5.50 | 16 |
| | 2 | 0.4230 | 0.0249 | 0.0826 | 0.1664 | ♂ | 0.45 | 100 | 20 | 4.00 | 7 |
| 14 (I:P) | | | | | Not germinated | | | | | | |
| 15 (U2:P) | 1 | 0.2055 | 0.0094 | 0.0294 | 0.0714 | ♂ | 0.76 | 220 | 31 | 6.00 | 14 |
| | 2 | 0.1564 | 0.0051 | 0.0200 | 0.0626 | ♂ | 0.98 | 197 | 19 | 5.00 | 15 |
| | 3 | 0.2094 | 0.0003 | 0.0339 | 0.0861 | ♀ | 0.73 | 170 | 23 | 5.00 | 16 |
| 16 (I:P) | 1 | 0.2335 | 0.0345 | 0.0393 | 0.1557 | ♀ | 0.54 | 180 | 31 | 4.00 | 23 |
| | 2 | 0.2043 | 0.0942 | 0.0332 | 0.2956 | ♀ | 0.62 | 170 | 30 | 6.00 | 19 |
| | 3 | 0.2997 | 0.0431 | 0.0053 | 0.1031 | ♂ | 0.59 | 160 | 26 | 6.00 | 18 |
| 17 (6:6) | 1 | 0.0136 | ND | 0.3823 | 0.1911 | ♂ | 0.76 | 160 | 30 | 6.00 | 18 |
| | 2 | 0.0109 | ND | 0.2387 | 0.1424 | ♂ | 1.04 | 153 | 32 | 6.00 | 14 |

TABLE 3-continued

Evaluation of main cannabinoid and morphological charateristic of F1 generation by selected crossing by artficial pollination.

| Plant name | Plant number | CBDA (%) | CBD (%) | THC (%) | THCA (%) | Gender | Stem diameter (cm) | Plant height (cm) | Leaf Length (cm) | Leaf width (cm) | Branch number |
|---|---|---|---|---|---|---|---|---|---|---|---|
| 18 (I:K2) | 1 | 1.3477 | 0.0881 | 0.0220 | 0.0695 | ♀ | 1.10 | 200 | 35 | 6.00 | 19 |
| | 2 | 0.2158 | 0.0004 | 0.0961 | 0.1242 | ♂ | 0.99 | 163 | 26 | 6.00 | 13 |
| 19 (I:K5) | 1 | 0.0058 | 0.0007 | 0.1900 | 0.2038 | ♂ | 0.82 | 170 | 30 | 6.00 | 17 |
| | 2 | 0.0041 | 0.0349 | 0.0712 | 0.1864 | ♂ | 0.68 | 157 | 24 | 6.00 | 16 |
| | 3 | 0.0075 | 0.0940 | 0.1318 | 0.1764 | ♀ | 0.73 | 150 | 30 | 6.00 | 16 |
| | 4 | 0.0079 | 0.0431 | 0.1847 | 0.1201 | ♂ | 0.97 | 143 | 23 | 5.00 | 16 |
| | 5 | 0.0039 | ND | 0.1134 | 0.1326 | ♂ | 0.84 | 132 | 30 | 6.00 | 14 |
| 20 (I:5) | 1 | 0.0051 | ND | 0.1760 | 0.1555 | ♀ | 1.09 | 135 | 35 | 6.00 | 18 |
| 21 (R28:K5) | | | | | | Not germinated | | | | | |
| 22 (I:5) | 1 | 0.3050 | 0.0665 | 0.1196 | 0.2815 | ♀ | 0.73 | 125 | 27 | 6.00 | 12 |
| | 2 | 0.0016 | 0.0783 | 0.1169 | 0.0059 | ♀ | 0.79 | 123 | 27 | 6.00 | 6 |
| | 3 | 0.0063 | 0.0574 | 0.1253 | 0.1776 | ♀ | 0.70 | 110 | 30 | 6.50 | 12 |
| 23 (U2:6) | 1 | 0.0118 | ND | 0.2413 | 0.1004 | ♀ | 1.17 | 176 | 26 | 7.00 | 16 |
| | 2 | 0.0105 | ND | 0.2653 | 0.1576 | ♂ | 0.86 | 170 | 34 | 7.00 | 20 |
| | 3 | 0.3263 | 0.0292 | 0.0564 | 0.1453 | ♀ | 0.83 | 167 | 27 | 6.00 | 14 |
| | 4 | 0.0056 | 0.0336 | 0.1852 | 0.1763 | ♂ | 0.89 | 148 | 26 | 6.00 | 18 |
| | 5 | 0.5951 | 0.0165 | 0.1026 | 0.1045 | ♀ | 0.85 | 145 | 31 | 6.50 | 16 |
| 24: (I:6) | 1 | 0.0017 | 0.0936 | 0.0730 | 0.1941 | ♂ | 1.25 | 227 | 41 | 8.00 | 15 |
| | 2 | 0.4227 | 0.0104 | 0.0549 | 0.0859 | ♀ | 1.25 | 205 | 39 | 8.00 | 16 |
| | 3 | 0.0042 | ND | 0.1268 | 0.1044 | ♂ | 1.31 | 215 | 41 | 7.00 | 19 |
| | 4 | 0.0073 | 0.0139 | 0.2082 | 0.1269 | ♀ | 1.25 | 195 | 42 | 8.00 | 14 |
| 25 (U2:K5) | 1 | 0.3322 | 0.0447 | 0.0681 | 0.1539 | ♀ | 0.94 | 150 | 28 | 7.00 | 16 |
| | 2 | 0.6012 | 0.0850 | 0.1102 | 0.0425 | ♂ | 0.87 | 133 | 39 | 7.00 | 16 |
| | 3 | 0.0067 | 0.0751 | 0.2228 | 0.5631 | ♂ | 0.60 | 120 | 27 | 6.00 | 13 |
| 26 (Li1:6) | 1 | 0.2498 | 0.0520 | 0.0485 | 0.0898 | ♂ | 0.90 | 185 | 38 | 6.00 | 15 |
| | 2 | 0.2497 | 0.0776 | 0.0376 | 0.3744 | ♂ | 0.63 | 156 | 30 | 5.00 | 17 |
| | 3 | 0.3084 | 0.0405 | 0.0539 | 0.0559 | ♂ | 0.71 | 137 | 28 | 5.00 | 19 |
| | 4 | 0.2562 | 0.0557 | 0.0413 | 0.0103 | ♀ | 0.90 | 126 | 26 | 5.00 | 15 |
| 27 (Li1:K5) | 1 | 0.4432 | 0.1333 | 0.0923 | 0.2956 | ♀ | 0.90 | 137 | 28 | 5.00 | 15 |
| | 2 | 0.2999 | 0.1393 | 0.1216 | 0.5732 | ♀ | 0.56 | 113 | 27 | 5.00 | 17 |
| | 3 | 0.2575 | 0.1140 | 0.0547 | 0.5213 | ♀ | 0.60 | 128 | 24 | 5.00 | 12 |
| | 4 | 0.3374 | 0.1096 | 0.0712 | 0.3220 | ♂ | 0.47 | 128 | 27 | 5.00 | 15 |

TABLE 4

Evaluation of main cannabinoid and morphological charateristic of F1 generation by selected crossing by artficial pollination.

| Plant name | Plant number | CBDA (%) | CBD (%) | THC (%) | THCA (%) | Gender | Stem diameter (cm) | Plant height (cm) | Leal Length (cm) | Leaf width (cm) | Branch number |
|---|---|---|---|---|---|---|---|---|---|---|---|
| | 5 | 0.2351 | 0.1646 | 0.0981 | 0.8008 | ♀ | 0.45 | 120 | 27 | 5.00 | 10 |
| 28 (U2:K2) | | | | | | Not germinated | | | | | |
| 29 (U1:K2) | 1 | 0.4828 | 0.0438 | 0.0076 | 0.1305 | ♀ | 0.74 | 126 | 29 | 5.00 | 17 |
| | 2 | 0.4358 | 0.0990 | 0.0089 | 0.1237 | ♂ | 0.62 | 125 | 28 | 6.00 | 19 |
| 30 (L1:5) | 1 | 0.2019 | 0.0004 | 0.0983 | 0.1489 | ♀ | 0.90 | 180 | 34 | 7.00 | 19 |
| | 3 | 0.0063 | ND | 0.1383 | 0.1567 | ♀ | 0.94 | 165 | 36 | 6.00 | 17 |
| | 4 | 0.2313 | ND | 0.1086 | 0.1527 | ♀ | 0.65 | 163 | 28 | 6.00 | 19 |
| | 5 | 0.3904 | 0.0015 | 0.1435 | 0.1364 | ♀ | 0.79 | 153 | 32 | 6.00 | 19 |
| 31 (R28:K2) | | | | | | Not germinated | | | | | |
| 32 (Li1:5) | | | | | | Not germinated | | | | | |
| 33 (I:P) | 1 | 0.2460 | 0.0004 | 0.0628 | 0.1117 | ♀ | 0.81 | 180 | 30 | 5.00 | 21 |
| | 2 | 0.0874 | 0.0046 | 0.0180 | 0.1136 | ♀ | 0.69 | 176 | 30 | 5.00 | 3 |
| | 3 | 0.0022 | 0.2603 | 0.0804 | 0.1325 | ♀ | 0.90 | 154 | 32 | 6.00 | 17 |
| 34 (I:U2) | 1 | 0.0088 | 0.0536 | 0.1876 | 0.5179 | ♂ | 0.90 | 160 | 32 | 6.00 | 17 |
| | 2 | 0.0036 | ND | 0.1612 | 0.2210 | ♂ | 0.97 | 157 | 33 | 6.00 | 18 |
| | 3 | 0.0172 | ND | 0.2781 | 0.0842 | ♀ | 0.74 | 120 | 28 | 6.00 | 18 |
| | 4 | 0.0022 | 0.0981 | 0.1274 | 0.3219 | ♂ | 0.86 | 112 | 25 | 5.00 | 8 |

After 5 weeks of cultivating female plants, excluding male plants, 10 $F_1$ generations were selected based on inflorescence production amount and total cannabidiol (CBD) content, and cannabinoid content in the inflorescence of the selected lines was measured (Table 5).

TABLE 5

Cannabinoid content of inflorescence in ten superial F1 generation (female)

| | Cannabinoid content (%) | | | |
|---|---|---|---|---|
| Strain | CBD | CBDA | Δ9-THC | Δ9-THCA |
| 12-2 | 0.0541 | 1.5009 | 0.0116 | 0.0261 |
| 12-4 | 0.0401 | 1.3442 | 0.1682 | 0.4563 |
| 13-1 | 0.0454 | 1.3476 | 0.1250 | 0.2767 |
| 18-1 | 0.1296 | 5.6419 | 0.0424 | 0.1357 |
| 22-1 | 0.1195 | 1.5297 | 0.3717 | 0.5932 |
| 23-3 | 0.1585 | 4.0208 | 0.3014 | 0.8757 |
| 23-5 | 0.1153 | 4.7567 | 0.2640 | 1.1260 |
| 24-2 | 0.1442 | 4.0796 | 0.2382 | 0.5457 |
| 27-1 | 0.0852 | 3.0160 | 0.3443 | 1.2854 |
| 30-5 | 0.0580 | 2.2370 | 0.4108 | 1.7433 |

The 18-1 line is a selective crossbred-line using the KHV2 genetic resource as seed parent and the India genetic resource as pollen parent (see Table 3). The results of cannabinoid content analysis of the parental lines grown under the same conditions are shown in Table 6. The 18-1 line was found to have a higher CBDA content in both leaves and inflorescence compared to the parental hemp resources.

TABLE 6

Cannabinoid content of India and KHV-2

| | | Cannabinoid content (%) | | | |
|---|---|---|---|---|---|
| Sample name | Type | CBDA | CBD | Δ9-THCA | Δ9-THC |
| India (fater plant) | Leaf | 0.29955 | 0.06306 | 0.01129 | 0.00041 |
| KHV-2 (mother plant) | Inflorescence | 2.06495 | 1.53064 | 0.02753 | 0.00626 |
| | Leaf | 0.83028 | 0.04779 | 0.01700 | 0.00021 |

The height and diameter of the hemp plant are advantageous for fiber production, but if excessive, there is a risk of lodging. The 18-1 line, which has the highest total cannabinoid content in leaves and inflorescence among all $F_1$ generations selected considering tree shape and plant height, and is applicable to smart farms, was selected as a favorable resource. After propagation based on nodal culture following the in vitro introduction, the 18-1 line was used for the evaluation of environmental adaptability (open field, greenhouse, and smart farm).

Example 2. In Vitro Introduction of Hemp Material

2-1. Preparation of Culture Medium

MS medium (Duchefa Biochemie, Haarlem, Netherlands) was taken in an amount of 4,405.19 mg and dissolved in 900 ml of distilled water. Thirty grams of sucrose (suitable for plant cell culture, Sigma-Aldrich Co., USA) were added thereto. Then, Meta-topolin (Duchefa Biochemie, Netherlands) was added such that it has a final concentration of 0.2 μM. After stirring, pH was adjusted to 5.75 using 1 N sodium hydroxide (DAEJUNG chemicals and metals Co., Ltd., Korea). After adjusting the volume to 1,000 ml, 4% of plant agar (Duchefa Biochemie) was additionally added. After that, the mixture was heated on a hot plate with stirring until it boils. The resultant was aliquoted in an amount of 50 ml to culture vessels and then subjected to autoclave under moisture condition at 151,988 Pa and 121 °C for 15 minutes. The resultant was allowed to solidify at room temperature (22±2 °C).

2-2. In Vitro Introduction of Hemp Explant

The inside of a clean bench was sterilized with an ultraviolet lamp and then sterilized again with 70% ethanol (DAEJUNG chemicals and metals Co., Ltd.). Nodes including the young leaves at the bottom part of the hemp were collected. They were transferred to a clean bench and placed in a sterilized glass bottle. Then, 70% ethanol was added and stirred for 30 seconds. After removing the ethanol and adding 30 ml of 2% sodium hypochlorite (Junsei Chemical Co., Ltd., Japan), polysorbate 20 (tween 20, Junsei Chemical Co., Ltd.) was added to the final concentration of 0.08% to 0.12%. Subsequently, washing was carried out by stirring for 15 minutes. After removing the solution, the resultant was washed six times with sterile distilled water. On a sterile Petri dish, the top part of the leaf was cut to have one node. After placing it on a culture medium, it was cultivated under LED light conditions of 18 h/day and temperature conditions of 23±2 °C. One month later, the regenerated in vitro plants were allowed to propagate in the same culture medium.

Example 3. Evaluation of Environmental Adaptability of Selected 18-1 Line

3-1. Evaluation of Environmental Adaptability of 18-1 Line Selected via Greenhouse Cultivation The greenhouse is located in Andong, South Korea, and topsoil was used as the culture soil. Line 18-1, which is the selected $F_1$ line, was planted in a pot (50 cm in diameter×70 cm in depth), and a white LED (35,201±401 lux) was used as a light source. Vegetative growth was induced by adjusting the photoperiod to 16/8 (light/dark) for 50 days after the planting, and flowering was induced by changing the photoperiod to 12/12 (light/dark) 50 days after the planting, while the culture temperature was maintained at 27±3 °C. For the 18-1 line grown in a closed greenhouse, CBD content was measured in leaves at 22, 59, 70, and 81 days after the plantation, and cannabinoid content was measured in inflorescence 9 days after the flowering treatment. The level of CBD content in the leaves showed a total CBD content of 0.70% immediately after the plantation, and 59 days after the plantation, which was the time of inflorescence appearance, the total CBD content was found to be 3.78%, showing a tendency to increase with the passage of plantation time, followed by a decrease upon the appearance of inflorescence. Total THC content was also found to show a similar tendency. The CBD content level in the inflorescence continued to increase from 59 days (i.e., the time of inflorescence appearance) to 81 days after the plantation, showing an increase to 5.09%, and the total THC content also increased up to 0.78% in the same period.

TABLE 7

| Cannabinoid content of F1 hybrid, 18-1 cultivated in closed green house | | | | | | |
|---|---|---|---|---|---|---|
| Days after transplanting | CBDA | CBD | Total CBD | Δ9-THC | Δ9-THCA | Total THC |
| | Leaf cannabinoid content (%) | | | | | |
| 0 | 0.6724 ± 0.3505 | 0.0265 ± 0.0189 | 0.6989 | 0.0080 ± 0.0028 | 0.0577 ± 0.0218 | 0.0657 |
| 22 | 0.6867 ± 0.0187 | 0.0072 ± 0.0013 | 0.6939 | 0.0087 ± 0.0005 | 0.1009 ± 0.0018 | 0.1096 |
| 59 | 3.6817 ± 0.3272 | 0.1055 ± 0.0047 | 3.7872 | 0.0429 ± 0.0061 | 0.3741 ± 0.0337 | 0.4170 |
| 70 | 1.4733 ± 0.3988 | 0.0470 ± 0.0078 | 1.5203 | 0.0190 ± 0.0018 | 0.2752 ± 0.0632 | 0.2942 |
| 81 | 1.6877 ± 0.3797 | 0.1237 ± 0.0693 | 1.8114 | 0.0288 ± 0.0072 | 0.1421 ± 0.0248 | 0.1709 |
| | Inflorescence cannabinoid content: (%) | | | | | |
| 0 | Not detected | | | | | |
| 22 | Not detected | | | | | |
| 59 | 3.7402 ± 0.4694 | 0.0704 ± 0.0327 | 3.8106 | 0.0316 ± 0.0044 | 0.5345 ± 0.0433 | 0.5661 |
| 70 | 3.9033 ± 0.8003 | 0.0623 ± 0.0226 | 3.9656 | 0.0292 ± 0.0015 | 0.3738 ± 0.0964 | 0.4030 |
| 81 | 4.9833 ± 0.7000 | 0.1086 ± 0.0383 | 5.0919 | 0.0378 ± 0.0195 | 0.7487 ± 0.2705 | 0.7865 |

The 18-1 line grown in a greenhouse showed a plant height of 99.3±8.5 cm and a growth diameter of 52.1±10.3 cm at the end of the vegetative growth period. Some of the 18-1 lines (about 20%) grown in greenhouses died, and it is contemplated that the death was caused by a failure to keep an appropriate level of VPD (vapor pressure deficit) under conditions of no ventilation and high light intensity provided by white LED lighting.

3-2. Evaluation of Environmental Adaptability of 18-1 Line Selected via Open Field Cultivation For open field cultivation, adaptability was evaluated in the open field environment of Andong City, South Korea (36°33' 56" N/128°43' 30" E). The cultivation period was from May 19, 2021 to Sep. 16, 2021 (average temperature 23 °C, no water irrigation, etc.). By having the 18-1 line grown in the open field as a subject, the flowering time point was selected under a short light condition in natural state after plantation, and it was divided into 48, 60, and 71 days. Then, the CBD content was measured in the leaves, and cannabinoid content was measured in the inflorescence of the flowered plant.

The level of CBD content in leaves did not change significantly after the planting to the open field, with total CBD content ranging from 2.5% to 3.3% and total THC content ranging from 0.23% to 0.30%, and the level of CBD content in inflorescence increased to, at 60 days after the planting, which is the time of inflorescence appearance, 9.98% and the total THC content increased to 0.50%. Furthermore, after 71 days, the total CBD content increased to 11.86% and the total THC content increased to 0.78%.

In addition, the 18-1 line grown in the open field showed a plant height of 207.5±10.3 cm and a growth diameter of 60.1±8.9 cm at the end of the vegetative growth period, showing excellent vegetative growth, and no dead plants were found.

The reason that the selected $F_1$ 18-1 line showed high cannabinoid content and excellent productivity in open field cultivation was due to the genetic predisposition of India and KHV2, which are the breeding parents of 18-1, and the good root zone development according to open field cultivation.

3-3. Evaluation of Environmental Adaptability of 18-1 Line Selected via Smart Farm Cultivation Smart farm cultivation was carried out using hydroponic cultivation using a 75 mm×75 mm growth block (Gordan Co., Reormond, Netherlands). The nutrient media solution was supplied once every 30 minutes for 30 seconds each time. The composition of the nutrient media solution is as shown in Table 10, and the LED conditions were brightness; 40,076±307 lux, PPFD; 692.4, PFD-R; 291.2, PFD-G; 254.8, PGF-B; It was 146.5. Vegetative growth was then induced by adjusting the photoperiod to 16/8 (light/dark) for 40 days after the planting, and flowering was induced by changing the photoperiod to 12/12 (light/dark) 40 days after the planting. The culture temperature was maintained at 27±3 °C.

TABLE 8

| Cannabinoid content of F1 hybrid, 18-1 cultivated in open field | | | | | | |
|---|---|---|---|---|---|---|
| Days after transplanting | CBDA | CBD | Total CBD | Δ9-THC | Δ9-THCA | Total THC |
| | Leaf cannabinoid content (%) | | | | | |
| 48 | 2.5412 ± 0.4978 | 0.0046 ± 0.0012 | 2.5458 | 0.0125 ± 0.0008 | 0.2243 ± 0.0380 | 0.2368 |
| 60 | 2.8765 ± 0.4765 | 0.0152 ± 0.0055 | 2.8917 | 0.0345 ± 0.0033 | 0.2548 ± 0.0454 | 0.2893 |
| 71 | 3.2674 ± 0.3354 | 0.1196 ± 0.0337 | 3.3870 | 0.0277 ± 0.0042 | 0.2728 ± 0.0382 | 0.3005 |
| | Inflorescence cannabinoid content (%) | | | | | |
| 48 | Not detected | | | | | |
| 60 | 9.5465 ± 1.1315 | 0.4409 ± 0.1875 | 9.9874 | 0.0547 ± 0.0155 | 0.4541 ± 0.0765 | 0.5088 |
| 71 | 11.4044 ± 1.1168 | 0.4640 ± 0.2156 | 11.8684 | 0.0777 ± 0.0190 | 0.7098 ± 0.0735 | 0.7875 |

TABLE 9

| Nutrient media solution of Smart farm in F1 hybrid, 18-1 cultivation | | | |
|---|---|---|---|
| Nutrient name | A solution (50 L) | B solution (50 L) | |
| $Ca(NO_3)\cdot 4H_2O$ | 1.50 kg | | A solution |
| $KNO_3$ | 3.79 kg | 3.79 kg | and B |
| $(NH_4)_2HPO_4$ | | 1.60 kg | solution were |
| $MgSO_4$ | | 4.30 kg | subjected to |
| Fe-EDTA | 460.0 g | | mixing to maintain |
| $MnSO_4$ | | 30.8 g | an EC range |
| $H_3BO_3$ | | 57.2 g | between 1.2 to 1.7 |
| $ZnSO_4$ | | 3.6 g | ($dSm^{-2}$), pH 6.0. |
| $CuSO_4$ | | 1.3 g | |
| $(NH_4)_6Mo_7O_{24}\cdot 4H_2O$ | | 0.4 g | |

By having the 18-1 line grown in the smart farm as a subject, CBD content was measured in leaves at 15, 31, 46, and 62 days, respectively, after the plantation, and cannabinoid content was measured in inflorescence 6 days after the flowering treatment.

It was found that the CBD content level in the leaves of 18-1, which is the $F_1$ line selected in the smart farm, gradually increased until 30 days after smart farm transplantation and was maintained at a constant level thereafter, while, with regard to the CBD content level in the inflorescence, the total CBD content increased to 5.38% and the total THC content increased to 0.45% after 46 days of the transplantation, which is the time point of the appearance of the inflorescence, and the total CBD content further increased to 11.70% and total THC content also further increased to 0.66% after 62 days, showing a level exceeding that of the cannabinoid content of the lines cultivated in greenhouse. In fact, the level was similar to that of cannabinoid content in open field cultivation.

Smart farms not only have the advantage of maintaining high security in many countries with restrictions in cultivating medical cannabis, including South Korea, but also have the advantage of not being limited by the seasons in a domestic environment with four distinct seasons, and easy pest control and accurate prediction of production.

The inventors of the present invention named the 18-1 line, which has a high cannabinoid content and is suitable for open field and smart farm cultivation, as Pinkpepper (*Cannabis sativa* L. cv. Pinkpepper).

Example 4. Development and Determination of Molecular Marker for Identifying Pinkpepper The inventors of the present invention analyzed the full-length genome of the new hemp cultivar Pinkpepper and assembled the genome (GenBank assembly GCA_029168945.1). Sequence analysis results of the three types of medical hemp (Cinderella story, Cherry blossom, Cloud berry), one type of textile hemp (Chungsam), and one type of marijuana hemp (Critical +2.0) were compared with the genome of the Pinkpepper cultivar, and nine sets of primers based on InDel (Insertion and Deletion) mutation were prepared.

gDNA was extracted from each young leaf of the hemp plant. After that, whole genome paired end re-sequencing was performed using Illumina's NovaSeq 6000, and low-quality bases with a phred score of 20 or lower were removed using the Tirmmomatic program (v. 0.39) to obtain the high-quality reads of at least 50 base pairs. After that, the trimmed data was mapped to the Pinkpepper genome using the mem option of the BWA program (v. 0.7.17-r1198) to select only the information of the hit reads, and, after

TABLE 10

| Cannabinoid content of Fl hybrid, 18-1 cultivated in Smart farm | | | | | | |
|---|---|---|---|---|---|---|
| Days after transplanting | CBDA | CBD | Total CBD | Δ9-THC | Δ9-THCA | Total THC |
| | Leaf cannabinoid content (%) | | | | | |
| 1 | 0.3921 ± 0.0793 | 0.0019 ± 0.0005 | 0.3940 | 0.0012 ± 0.0000 | 0.0245 ± 0.0041 | 0.0257 |
| 15 | 2.4700 ± 0.5014 | 0.0399 ± 0.0143 | 2.5099 | 0.0237 ± 0.0144 | 0.1196 ± 0.0105 | 0.1433 |
| 31 | 3.0571 ± 0.0791 | 0.1464 ± 0.0588 | 3.2035 | 0.0272 ± 0.0035 | 0.1546 ± 0.0043 | 0.1818 |
| 46 | 2.2613 ± 0.0177 | 0.0201 ± 0.0072 | 2.2814 | 0.0130 ± 0.0025 | 0.0974 ± 0.0219 | 0.1104 |
| 62 | 2.5948 ± 0.5553 | 0.0545 ± 0.0472 | 2.6493 | 0.0113 ± 0.0002 | 0.0999 ± 0.0169 | 0.1112 |
| | Inflorescence cannabinoid content (%) | | | | | |
| 1 | Not detected | | | | | |
| 15 | Not detected | | | | | |
| 31 | Not detected | | | | | |
| 46 | 5.3462 ± 0.6432 | 0.0363 ± 0.0161 | 5.3825 | 0.0081 ± 0.0032 | 0.4394 ± 0.0839 | 0.4475 |
| 62 | 11.3610 ± 0.3412 | 0.3416 ± 0.2194 | 11.7026 | 0.0270 ± 0.0033 | 0.6421 ± 0.0741 | 0.6691 |

In addition, the 18-1 line grown in the smart farm had a plant height of 101±10.8 cm at the end of the vegetative growth period, which was half the plant height of the open field cultivation, and a growth diameter of 58.1±9.9 cm, which was similar to the open field cultivation. Smart farm cultivation of the selected $F_1$ line 18-1 showed the characteristics of high cannabinoid content and low plant height, indicating that it can be suitably used for cultivation in smart farms.

removing the duplicate bases, the coverage genome was assembled from mapping of the 6 types of hemp samples. Thereafter, mutation detection and filtering were performed using the GATK program (v. 4.3.0.0), and, for InDel mutation, the location within the gene region, transcript, and information of the coding protein were determined using the SnpEff program (v. 5.0e). After adding annotations, primer sets were prepared for the corresponding mutations by using Primer3.

TABLE 11

Nine primer sets selected under in silico conditions

| Primer name | Chromosome No. | InDel difference (bp) | Primer (5'-3') | Product size (bp) | Effect Impact[1)] |
|---|---|---|---|---|---|
| InDel1 | 3 | 53 | F: CTT TAA CTG GCT TGG AGA TTG C (SEQ ID NO: 1)<br>R: GAT CAT TCT TGC TCT AGG TGC T (SEQ ID NO: 2) | 444 | High |
| InDel2 | 6 | 83 | F: ATT GGA TTG GAG CTG TTT GGT G (SEQ ID NO: 3)<br>R: CGC TTT CGA ATG GAT ATC TCC T (SEQ ID NO: 4) | 332 | High |
| InDel3 | X(10) | 50 | F: CTG GAT GTG GAG ACT CAA GTT T (SEQ ID NO: 5)<br>R: AGA ATG GAC TGG CTT AGT ATG C (SEQ ID NO: 6) | 333 | Modifier |
| InDel4 | X(10) | 101 | F: ACC CTC GTG TAA GTA GCT CTT A (SEQ ID NO: 7)<br>R: CTG GTT CCT TGA GAG GCT TTA A (SEQ ID NO: 8) | 389 | Modifier |
| InDel5 | 1 | 62 | F: CAT GCT AGA GGG TGA ACG TAA A (SEQ ID NO: 9)<br>R: CCA ACA TAG CAA TTG AGT GTG C (SEQ ID NO: 10) | 484 | Modifier |
| InDel6 | 1 | 91 | F: CGC CAT CCA ACA GAT CAT CTA A (SEQ ID NO: 11)<br>R: CGA TGA CGA AAC CTT GTT ACT C (SEQ ID NO: 12) | 411 | Modifier |
| InDel7 | 3 | 50 | F: CTC CTG CAA TCA ACT GTA CTC A (SEQ ID NO: 13)<br>R: ATT CAA CAT GGC TCT CAT CCT C (SEQ ID NO: 14) | 328 | Modifier |
| InDel8 | 3 | 60 | F: TCT CTC TAC ATC AAG GTC CGA A (SEQ ID NO: 15)<br>R: CCA TGA TTG ATG GCT ATA GAG C (SEQ ID NO: 16) | 337 | Modifier |
| InDel9 | Un-scaffolded | 71 | F: TAT TCC CGA AGT TGT GTT G SEQ ID NO: 17)<br>R: TGT GGC AAT CTA GAC CTA TGA C (SEQ ID NO: 18) | 456 | Modifier |

[1)]There are 4 types of effectiveness for SnpEff annotations. High: For mutations that have a significant effect on the protein. Moderate: For mutations that can modify the effect of the protein. Modifier: For mutations whose effect on the protein is unpredictable or for which there is no evidence. Low: For mutations that are not expected to affect the protein.

Using the 9 primer sets selected under in silico conditions, PCR was performed on 6 cultivars and the $F_1$ generation of Pinkpepper (Pinkpepper×Chungsam, open pollinated) to evaluate the applicability of InDel primers. PCR was performed by using, for a total volume of 50 μl, a mixture of 5.0 μl of 10× reaction buffer, 1.0 μl of 10 mM stabilized dNTP, 1.0 μl each of 20 μM forward and reverse primers, 2.0 μl of 10 ng/μl gDNA template, 39.5 μl of sterile ultrapure water, and 0.5 μl of Taq polymerase. By using Thermal Cycler Dice Touch (TP350, TAKARA bio Inc., Japan), an initial denaturation process was performed at 94 °C for 3 minutes, and denaturation at 94 °C for 30 seconds, gradient annealing at ±5 °C of Tm (melting temperature) of the primer for 30 seconds, and extension at 72 °C for 60 seconds were repeated 30 times. Finally, additional extension was performed at 72 °C for 7 minutes. PCR products were identified using a 3% agarose gel.

Figure 4A:
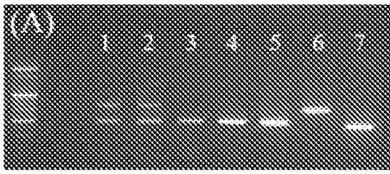
FIGS. 4A to 4I show the in vitro assay results of nine primer sets (Table 11) selected under in silico conditions.
Figure 4B:
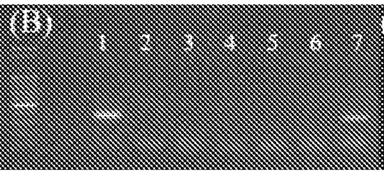
Figure 4C:
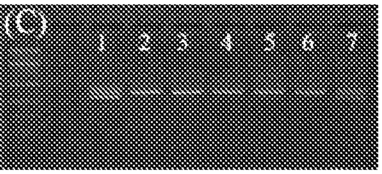
Figure 4D:
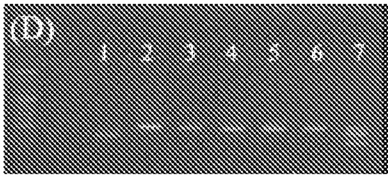
Figure 4E:
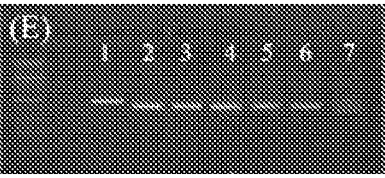
Figure 4F:
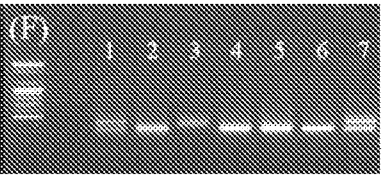
Figure 4G:
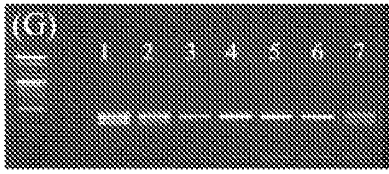
Figure 4H:
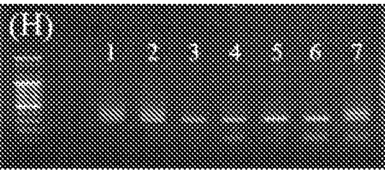
Figure 4I:
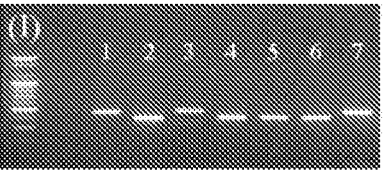

As a result of performing PCR using gradient PCR and setting the optimal binding temperature at Tm±5 °C, the InDel1 primer was found to have insufficient identification ability as a Pinkpepper-like band appeared in Chungsam cultivar (FIG. 4A). The InDel2 primer was found to be capable of identifying the Pinkpepper and $F_1$ generation, but, as yielding no amplification for other cultivars, showed the characteristics of a dominant marker rather than a co-dominant marker unique to InDel (FIG. 4B). In the case of the InDel3 primer, a Pinkpepper-specific band was not formed (FIG. 4C). In the case of the InDel6 primer, a Pinkpepper-specific band was observed in the Cinderella story cultivar (FIG. 4F), and, in the case of the InDel7 and InDel8 primers, a Pinkpepper-specific band was observed in the Critical +2.0 cultivar (FIGS. 4G and 4H). In the case of the InDel9 primer, a Pinkpepper-specific band was observed in the Cinderella story cultivar (FIG. 4I), and thus it was found that only InDel4 and InDel5 primers are capable of identifying Pinkpepper and Pinkpepper $F_1$ generation from other hemp cultivars (FIGS. 4D and 4E).

Finally, the optimal binding temperature of the InDel4 primer was set to 53.2 °C, and the optimal binding temperature of the InDel5 primer was set to 60.0 °C.

Figure 5A:
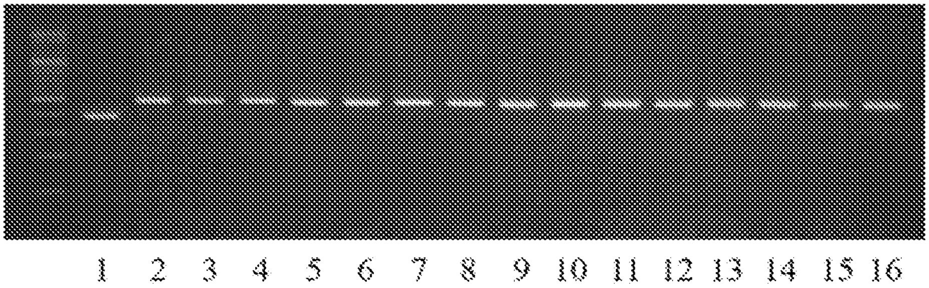
FIGS. 5A and 5B show the identification results of Pinkpepper cultivars using the InDel4 marker (FIG. 5A) and the InDel5 marker (FIG. 5B). Lane 1: Pinkpepper, Lane 2: Critical +2.0, Lane 3: Cinderella story, Lane 4: Cherry blossom, Lane 5: Cloud berry, Lane 6: Queen dream, Lane 7: Apricot auto, Lane 8: Cherry blonde, Lane 9: WV, Lane 10: Spectrum, Lane 11: Chungsam, Lane 12: Pinkpepper, Lane 13: India native, Lane 14: UK native, Lane 15: Portugal native, and Lane 16: Italy native, marker: 100 bp.
Figure 5B:
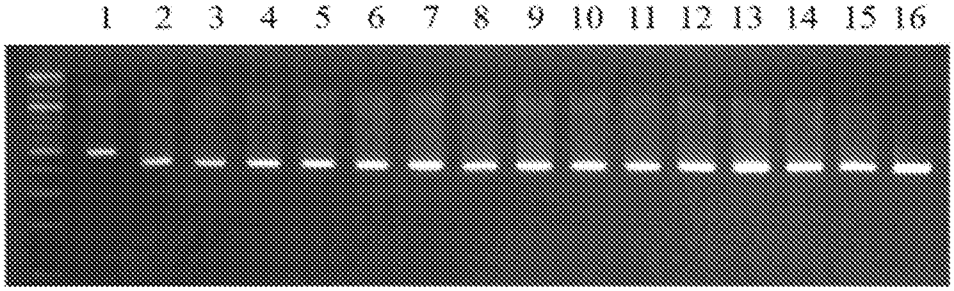

Using marijuana hemp grown for other purposes (Critical 2.0+), hemp for medical use (Cinderella story, Cherry blossom, Cloud berry, Queen dream, Apricot auto, Cherry blonde, WV, Spectrum, Pinkpepper), and hemp for obtaining fibers (Chungsam), wild type hemp (India, UK, Portugal, Italy), PCR was performed with InDel4 and InDel5 primers under the same conditions as above, and the bands were determined through electrophoresis. As a result, the InDel4 primer showed a band that distinguishes Pinkpepper from 15 other cultivars (FIG. 5A), and, compared to the DNA ladder, the Pinkpepper cultivar was found to produce an amplicon of about 400 bp while the other cultivars produce an amplicon of about 500 bp. The InDel5 primer also showed a band that distinguishes Pinkpepper from 15 other cultivars (FIG. 5B) and it was found that the Pinkpepper cultivar produces an amplicon of about 500 bp and that the other cultivars produce an amplicon of about 400 bp. As a result, when determined in vitro, it was found that the InDel4 primer could detect a Pinkpepper cultivar-specific deletion and the InDel5 primer could detect a Pinkpepper cultivar-specific insertion mutation.

To accurately determine the nucleotide sequence and size of the PCR amplicon, Sanger sequencing was carried out. The PCR product was purified using Sephadex (GE Healthcare, USA) and then cycle-sequencing was performed using BigDye terminator v3.1 cycle sequencing kit (Thermo-Fisher Scientific Inc., USA). After secondary purification, nucleotide sequencing was carried out by using ABI 3730XL DNA Analyzer (Thermo-Fisher Scientific Inc.). The sequencing results (.abl file) were then subjected to the analysis of bioinformatics using CLC genomics workbench (QIAGEN, Netherlands).

As a result of sequencing the PCR product using the InDel4 primer, the Pinkpepper cultivar was found to have a nucleotide sequence of 391 bp, showing a difference of about 116 bp from the 15 other cultivars, which were about 507 bp in length. The PCR amplicon sequence of InDel4, which has 391 bp, was found to be 99.4% identical to the corresponding part in the assembled genome. Furthermore, as the size difference from the predicted amplicon was found to be due to the slight deletion of the binding part of the forward primer which is caused by the trimming algorithm, it is believed to have high homology with the assembled genome in actual in vitro application.

As a result of sequencing the PCR product based on the InDel5 primer, the Pinkpepper cultivar was found to have a nucleotide sequence of 461 bp, while the other cultivars have a nucleotide sequence of about 408 bp, showing a difference of about 53 bp from the Pinkpepper cultivar. The PCR amplicon sequence of InDel5, which has 461 bp, was found to be 99.3% identical to the corresponding part in the assembled genome. The size difference from the predicted amplicon was found to be due to the slight deletion of the binding part of the forward and reverse primers which is caused by the trimming algorithm, and thus it is believed to have high homology with the assembled genome in actual in vitro application, like the InDel4 primer.

Example 5. Determination of Possibility of Using Established InDel Markers for Identifying Later Generations In order to determine whether the next generation of Pinkpepper can be selected using the InDel4 and InDel5 markers that have been to found to identify the Pinkpepper cultivar from 15 other cultivars, PCR was performed under the same conditions as above and the bands were examined through electrophoresis.

As the later generation of Pinkpepper, the feminized seeds produced by a silver nitrate treatment of the Pinkpepper seed parent and the $F_1$ generation obtained by crossing between Pinkpepper and Chungsam based on open pollination were used.

Figure 6A:
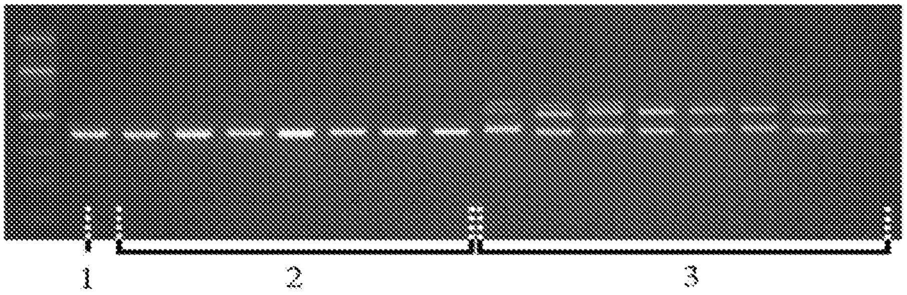
FIGS. 6A and 6B show the verification results of subsequent generation of the Pinkpepper cultivar using the InDel4 marker (FIG. 6A) and InDel5 marker (FIG. 6B). 1: Pinkpepper seed parent, cluster 2: Pinkpepper derived from feminized seed, cluster 3: Pinkpepper×Chungsam $F_1$ generation (open pollinated).
Figure 6B:
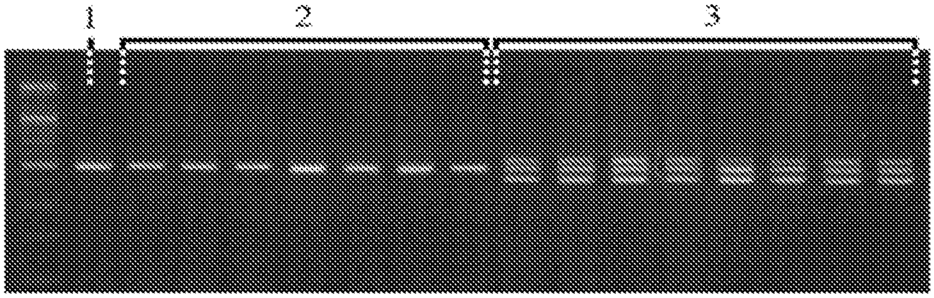

As a result, in the case of the InDel4 marker, it was found that the mutation was conservatively inherited to both the feminized seeds and open pollination seeds and the both have a specific band of less than 400 bp, which is the same as that of the Pinkpepper seed parent (FIG. 6A). The InDel5 marker also showed a specific band of approximately 500 bp, which is identical to the Pinkpepper seed parent, suggesting that, based on the feminized seeds and open pollination seeds, it can be used for identifying the $F_1$ generation having Pinkpepper as seed parent (FIG. 6B).

What is claimed is:

1. A hemp cultivar Pinkpepper (*Cannabis sativa* L. cv. Pinkpepper) plant, representative feminized seed of which was deposited under Accession Number KACC 88008BP.

2. A feminized seed obtained by induction of a male flower on a female plant of the hemp cultivar Pinkpepper plant of claim 1.

3. A $F_1$ hemp plant produced by crossing the hemp cultivar Pinkpepper plant of claim 1 with other hemp cultivar.

4. A seed of the $F_1$ hemp plant according to claim 3.

5. A transgenic hemp plant obtained by transformation of the hemp cultivar Pinkpepper plant of claim 1.

* * * * *

SEQUENCE LISTING

```
Sequence total quantity: 18
SEQ ID NO: 1          moltype = DNA  length = 22
FEATURE               Location/Qualifiers
misc_feature          1..22
                      note = InDel1_forward primer
source                1..22
                      mol_type = other DNA
                      organism = synthetic construct
SEQUENCE: 1
ctttaactgg cttggagatt gc                                22

SEQ ID NO: 2          moltype = DNA  length = 22
FEATURE               Location/Qualifiers
misc_feature          1..22
                      note = InDel1_reverse primer
source                1..22
                      mol_type = other DNA
                      organism = synthetic construct
SEQUENCE: 2
gatcattctt gctctaggtg ct                                22

SEQ ID NO: 3          moltype = DNA  length = 22
FEATURE               Location/Qualifiers
misc_feature          1..22
                      note = InDel2_forward primer
```

```
source                 1..22
                       mol_type = other DNA
                       organism = synthetic construct
SEQUENCE: 3
attggattgg agctgtttgg tg                                            22

SEQ ID NO: 4           moltype = DNA  length = 22
FEATURE                Location/Qualifiers
misc_feature           1..22
                       note = InDel2_reverse primer
source                 1..22
                       mol_type = other DNA
                       organism = synthetic construct
SEQUENCE: 4
cgctttcgaa tggatatctc ct                                            22

SEQ ID NO: 5           moltype = DNA  length = 22
FEATURE                Location/Qualifiers
misc_feature           1..22
                       note = InDel3_forward primer
source                 1..22
                       mol_type = other DNA
                       organism = synthetic construct
SEQUENCE: 5
ctggatgtgg agactcaagt tt                                            22

SEQ ID NO: 6           moltype = DNA  length = 22
FEATURE                Location/Qualifiers
misc_feature           1..22
                       note = InDel3_reverse primer
source                 1..22
                       mol_type = other DNA
                       organism = synthetic construct
SEQUENCE: 6
agaatggact ggcttagtat gc                                            22

SEQ ID NO: 7           moltype = DNA  length = 22
FEATURE                Location/Qualifiers
misc_feature           1..22
                       note = InDel4_forward primer
source                 1..22
                       mol_type = other DNA
                       organism = synthetic construct
SEQUENCE: 7
accctcgtgt aagtagctct ta                                            22

SEQ ID NO: 8           moltype = DNA  length = 22
FEATURE                Location/Qualifiers
misc_feature           1..22
                       note = InDel4_reverse primer
source                 1..22
                       mol_type = other DNA
                       organism = synthetic construct
SEQUENCE: 8
ctggttcctt gagaggcttt aa                                            22

SEQ ID NO: 9           moltype = DNA  length = 22
FEATURE                Location/Qualifiers
misc_feature           1..22
                       note = InDel5_forward primer
source                 1..22
                       mol_type = other DNA
                       organism = synthetic construct
SEQUENCE: 9
catgctagag ggtgaacgta aa                                            22

SEQ ID NO: 10          moltype = DNA  length = 22
FEATURE                Location/Qualifiers
misc_feature           1..22
                       note = InDel5_reverse primer
source                 1..22
                       mol_type = other DNA
                       organism = synthetic construct
SEQUENCE: 10
ccaacatagc aattgagtgt gc                                            22

SEQ ID NO: 11          moltype = DNA  length = 22
FEATURE                Location/Qualifiers
misc_feature           1..22
```

```
                         note = InDel6_forward primer
source                   1..22
                         mol_type = other DNA
                         organism = synthetic construct
SEQUENCE: 11
cgccatccaa cagatcatct aa                                        22

SEQ ID NO: 12            moltype = DNA  length = 22
FEATURE                  Location/Qualifiers
misc_feature             1..22
                         note = InDel6_reverse primer
source                   1..22
                         mol_type = other DNA
                         organism = synthetic construct
SEQUENCE: 12
cgatgacgaa accttgttac tc                                        22

SEQ ID NO: 13            moltype = DNA  length = 22
FEATURE                  Location/Qualifiers
misc_feature             1..22
                         note = InDel7_forward primer
source                   1..22
                         mol_type = other DNA
                         organism = synthetic construct
SEQUENCE: 13
ctcctgcaat caactgtact ca                                        22

SEQ ID NO: 14            moltype = DNA  length = 22
FEATURE                  Location/Qualifiers
misc_feature             1..22
                         note = InDel7_reverse primer
source                   1..22
                         mol_type = other DNA
                         organism = synthetic construct
SEQUENCE: 14
attcaacatg gctctcatcc tc                                        22

SEQ ID NO: 15            moltype = DNA  length = 22
FEATURE                  Location/Qualifiers
misc_feature             1..22
                         note = InDel8_forward primer
source                   1..22
                         mol_type = other DNA
                         organism = synthetic construct
SEQUENCE: 15
tctctctaca tcaaggtccg aa                                        22

SEQ ID NO: 16            moltype = DNA  length = 22
FEATURE                  Location/Qualifiers
misc_feature             1..22
                         note = InDel8_reverse primer
source                   1..22
                         mol_type = other DNA
                         organism = synthetic construct
SEQUENCE: 16
ccatgattga tggctataga gc                                        22

SEQ ID NO: 17            moltype = DNA  length = 22
FEATURE                  Location/Qualifiers
misc_feature             1..22
                         note = InDel9_forward primer
source                   1..22
                         mol_type = other DNA
                         organism = synthetic construct
SEQUENCE: 17
tattcctccc gaagttgtgt tg                                        22

SEQ ID NO: 18            moltype = DNA  length = 22
FEATURE                  Location/Qualifiers
misc_feature             1..22
                         note = InDel9_reverse primer
source                   1..22
                         mol_type = other DNA
                         organism = synthetic construct
SEQUENCE: 18
tgtggcaatc tagacctatg ac                                        22
```